United States Patent [19]

Ligon

[11] Patent Number: 4,469,642

[45] Date of Patent: Sep. 4, 1984

[54] CONDENSATION OF RING-SUBSTITUTED PHENYLACETONITRILES WITH MONO-ESTERS OF DICARBOXYLIC ACIDS

[75] Inventor: Robert C. Ligon, Raleigh, N.C.

[73] Assignee: Union Carbide Corporation, Danbury, Conn.

[21] Appl. No.: 480,726

[22] Filed: Mar. 31, 1983

[51] Int. Cl.$^3$ ............................................ C07C 121/76
[52] U.S. Cl. ................................................ 260/465 D
[58] Field of Search .................................... 260/465 D

[56] References Cited

U.S. PATENT DOCUMENTS 4,175,135  11/1979  Haines ................................ 424/311
4,256,657  3/1981  Wheeler .......................... 260/465 D
4,422,870  12/1983  Wheeler ................................ 71/106

*Primary Examiner*—Dolph H. Torrence
*Attorney, Agent, or Firm*—J. A. Shedden

[57] ABSTRACT

This invention relates to the stoichiometric condensation of substituted phenylacetonitriles with mono-esters of dibasic carboxylic acids. Use of the mono-ester results in substantially purer product by eliminating the bis-condensation observed with use of the diester reactant. The resulting cyano-keto-acids are obtained in good yield and can be used to prepare biologically active 2-aryl-1,3-cyclohexanediones without elaborate purification.

10 Claims, No Drawings

CONDENSATION OF RING-SUBSTITUTED PHENYLACETONITRILES WITH MONO-ESTERS OF DICARBOXYLIC ACIDS

FIELD OF THE INVENTION

This invention relates to a novel method of preparing cyano-keto-acids from the stoichiometric condensation of substituted phenylacetonitriles with mono-esters of dicarboxylic acids.

BACKGROUND OF THE INVENTION

Certain 2-aryl-1,3-cyclohexanediones and their esters are known to be extremely active, biological compounds. U.S. Pat. Nos. 4,175,135 and 4,256,657 and copending application U.S. Ser. No. 781,781 filed Mar. 28, 1977, now U.S. Pat. No. 4,422,870, all of which are herein incorporated by reference, teach the usefulness of these compounds as herbicidal and miticidal agents and as agents for orally controlling acarina ectoparasites on warm-blooded animals.

Cyano-keto-acids, such as the 6-aryl-6-cyano-5-ketohexanoic acids and/or their esters are important intermediates in the manufacture of the afore-described 2-aryl-1,3-cyclohexanediones.

U.S. Pat. No. 4,256,657 teaches that the coupling of ring-substituted phenylacetonitriles with diesters of alkyl-substituted glutaric acid in a basic medium will result in esters of the cyano-keto-acids described above, e.g. Example XVI of said patent; however, a significant disadvantage to this process is the large molar excess (50 to 200%) of glutaric acid diester required to suppress reaction of a second molecule of ring-substituted phenylacetonitrile with the desired product.

SUMMARY OF THE INVENTION

In accordance with the present invention, it has been discovered that good yields of cyano-keto-acids can be realized by the stoichiometric coupling of ring-substituted phenylacetonitriles with mono-esters of substituted glutaric acid.

Furthermore, the resulting substituted hexanoic acid may be incorporated directly into the prior art process of U.S. Pat. No. 4,175,135 for the production of 2-aryl-1,3-cyclohexanediones.

DETAILED DESCRIPTION OF THE INVENTION

The invention relates to the discovery that ring-substituted phenylacetonitriles can be stoichiometrically coupled with mono-esters of substituted glutaric acid to produce cyano-keto-hexanoic acids in good yields.

Specifically, the invention relates to the discovery that compounds of the formula can be prepared in good yield by reacting a phenylacetonitrile of the formula:

wherein
Z, Z', Z" and Z''' are individually hydrogen, nitro, polyhaloalkyl, halogen, cyano, alkyl, alkoxy, alkylthio, alkylsulfinyl, alkylsulfonyl, alkanoyl, amido, amino, or haloalkyl; and
$R_1$ is alkyl, halogen, polyhaloalkyl, or haloalkyl;
with a stoichiometric amount of a compound of the formula:

wherein
$R_2$, $R_3$, $R_4$, $R_5$, $R_6$ and $R_7$ are individually hydrogen or either substituted or unsubstituted alkyl or phenyl wherein the permissible substituents are one or more alkyl, cyano, halogen, nitro, alkoxy, alkylthio, alkylsulfinyl, alkylsulfonyl, or dialkylamino substituents or any two $R_2$, $R_3$, $R_4$, $R_5$, $R_6$ or $R_7$ substituents together may form an alkylene or alkenylene chain having from 2 to 20 carbon atoms completing a 3, 4, 5, 6 or 7 membered ring structure;
with the proviso that $R_1$, $R_2$, $R_3$, $R_4$, $R_5$, $R_6$, $R_7$, Z, Z', Z" and Z''' substituents individually may not include more than ten aliphatic carbon atoms; and $R_8$ is substituted or unsubstituted alkyl;
in the presence of a base and a non-protic solvent at a temperature of from about 60° C. to about 150° C.

Although the temperature and pressure of the process are not critical, it is preferred to operate at from about 100° C. to about 140° C. and most preferably from about 120° C. to about 135° C. at atmospheric pressure.

Preferred substituents in the reactions of this invention, primarily because of the high miticidal effects realized in the 2-substituted-1,3-cyclohexanediones derived from the intermediates of this invention, are the following:

Z, Z', Z" and Z''' are individually hydrogen, alkyl, cyano, alkoxy, halogen, or trihalomethyl;
$R_1$ is alkyl or halogen; and $R_2$, $R_3$, $R_4$, $R_5$, $R_6$ and $R_7$ are individually hydrogen or alkyl; and
$R_8$ is $C_1$ to $C_5$ alkyl.

The most preferred substituents are the following:
Z, Z', Z" and Z''' are individually hydrogen, methyl, methoxy, cyano, or halogen;
$R_1$ is methyl or halogen; and
$R_2$, $R_3$, $R_4$, $R_5$, $R_6$ and $R_7$ are individually hydrogen, methyl or ethyl; and $R_8$ is ethyl.

Illustrative of the strong bases which are useful in the reactions of this invention are the metal alkoxides, alkali metal amides, alkali metal hydrides or mixtures of these bases.

The preferred base is sodium ethoxide.

It is also preferred that at least two equivalents of base be present during the reaction.

Illustrative of the non-protic solvents which are useful in this invention are the aromatic hydrocarbons, cyclic and acylic ethers, dimethyl sulfoxide, dimethylformamide, and sulfolane. The preferred non-protic solvents are dimethoxyethane, tetrahydrofuran, n-butyl ether, dioxane and xylene.

The following example is set forth for purposes of illustration so that those skilled in the art may better understand the invention, and it should be understood that it is not to be construed as limiting this invention in any manner.

EXAMPLE I

Preparation of 6-cyano-3,3-dimethyl-5-keto-6-(2-methylphenyl)hexanoic acid

To a solution of sodium ethoxide in o-xylene; prepared by adding 25 ml ethanol to 5.0 g sodium metal in 100 ml o-xylene, heating to reflux for 1 hour, and distilling out the excess ethanol; was added 13.1 g 2-methylphenylacetonitrile and 18.8 g ethyl 3,3-dimethylglutarate in 50 ml o-xylene. The reaction temperature was held at 140° C. by distilling out ethanol as formed, and heating for 3 hours with vigorous stirring. The mixture was cooled to ambient temperature and 100 ml cold water added. The layers were separated and the organic layer extracted once with 50 ml 10% aqueous sodium hydroxide. The combined aqueous layer was washed once with 75 ml diethyl ether, then acidified to pH 2 with concentrated sulfuric acid. The product was isolated by extracting twice with 75 ml diethyl ether, washing the ether solution with 50 ml saturated NaCl solution, drying over magnesium sulfate and vacuum stripping the product. The crude product weighed 22.36 g and contained 85.41 wt. % 6-cyano-3,3-dimethyl-5-keto-6-(2 methylphenyl)hexanoic acid by HPLC assay.

I claim:

1. A method of preparing a compound of the formula:

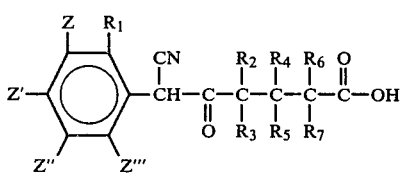

which comprises:
reacting a compound of the formula

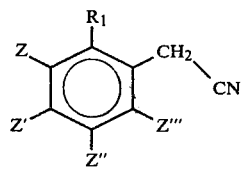

wherein $Z$, $Z'$, $Z''$ and $Z'''$ are individually hydrogen, nitro, polyhaloalkyl, halogen, cyano, alkyl, alkoxy, alkylthio, alkylsulfinyl, alkylsulfonyl, alkanoyl, amido, amino, or haloalkyl; and $R_1$ is alkyl, halogen, polyhaloalkyl, or haloalkyl;

with a compound of the formula:

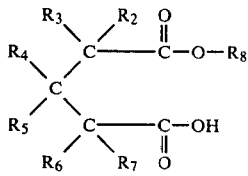

wherein $R_2$, $R_3$, $R_4$, $R_5$, $R_6$ and $R_7$ are individually hydrogen or either substituted or unsubstituted alkyl or phenyl wherein the permissible substituents are one or more alkyl, cyano, halogen, nitro, alkoxy, alkylthio, alkylsulfinyl, alkylsulfonyl, or dialkylamino substituents or any two $R_2$, $R_3$, $R_4$, $R_5$, $R_6$ or $R_7$ substituents together may form an alkylene or alkenylene chain having from 2 to 20 carbon atoms completing a 3, 4, 5, 6 or 7 membered ring structure;

with the proviso that $R_1$, $R_2$, $R_3$, $R_4$, $R_5$, $R_6$, $R_7$, $Z$, $Z'$, $Z''$ and $Z'''$ substituents individually may not include more than ten aliphatic carbon atoms; and $R_8$ is substituted or unsubstituted alkyl;

in the presence of a base and a non-protic solvent.

2. The method according to claim 1 wherein $Z$, $Z'$, $Z''$ and $Z'''$ are individually hydrogen, alkyl, cyano, alkoxy, halogen, or trihalomethyl;
$R_1$ is alkyl or halogen; and $R_2$, $R_3$, $R_4$, $R_5$, $R_6$ and $R_7$ are individually hydrogen or alkyl; and $R_8$ is $C_1$–$C_5$ alkyl.

3. The method according to claim 2 wherein $Z$, $Z'$, $Z''$ and $Z'''$ are individually hydrogen, methyl, methoxy, cyano, or halogen;
$R_1$ is methyl or halogen; and $R_2$, $R_3$, $R_4$, $R_5$, $R_6$ and $R_7$ are individually hydrogen, methyl or ethyl; and $R_8$ is ethyl.

4. The method according to claim 1 wherein said base comprises a metal alkoxide, alkali metal amide, alkali metal hydride or mixtures thereof.

5. The method according to claim 4 wherein said base comprises sodium ethoxide.

6. The method according to claim 4 wherein said base comprises sodium amide.

7. The method according to claim 1 wherein said non-protic solvent is selected from the group consisting of aromatic hydrocarbons, cyclic ethers, acyclic ethers, dimethyl sulfoxide, dimethylformamide, and sulfolane.

8. The method according to claim 7 wherein said non-protic solvent is selected from the group consisting of dimethoxyethane, tetrahydrofuran, n-butyl ether, dioxane and xylene.

9. The method according to claim 1 wherein the reaction temperature is from about 60° C. to about 150° C. at atmospheric pressure.

10. The method according to claim 9 wherein the reaction temperature is from about 100° C. to 140° C.

* * * * *